(12) United States Patent
Schatzberg et al.

(10) Patent No.: US 7,326,697 B2
(45) Date of Patent: Feb. 5, 2008

(54) METHODS FOR INCREASING THE THERAPEUTIC RESPONSE TO ELECTROCONVULSIVE THERAPY

(75) Inventors: Alan F. Schatzberg, Los Altos, CA (US); Joseph K. Belanoff, Woodside, CA (US)

(73) Assignee: Corcept Therapeutics, Inc., Menlo Park, CA (US)

( * ) Notice: Subject to any disclaimer, the term of this patent is extended or adjusted under 35 U.S.C. 154(b) by 737 days.

(21) Appl. No.: 10/411,503

(22) Filed: Apr. 8, 2003

(65) Prior Publication Data

US 2004/0029849 A1    Feb. 12, 2004

Related U.S. Application Data

(60) Provisional application No. 60/376,814, filed on Apr. 29, 2002.

(51) Int. Cl.
*A61K 31/56* (2006.01)
(52) U.S. Cl. ........................ 514/178; 514/179
(58) Field of Classification Search ................ 514/178, 514/179
See application file for complete search history.

(56) References Cited

U.S. PATENT DOCUMENTS 4,873,981 A    10/1989    Abrams et al.
6,150,349 A *  11/2000    Schatzberg et al. ......... 514/179
6,362,173 B1   3/2002     Schatzberg et al.
6,369,046 B1   4/2002     Schatzberg et al.

OTHER PUBLICATIONS

Cadieux, "Practical Management of Treatment-resistant Depression" in American Family Physician, Dec. 1999,vol. 58, No. 9.*
Sackeim, "Central Issues Regarding the Mechanisms of Action of Electroconvulsive Therapy: Directions for Future Research", *Psychopharmacology Bulletin* 30:3: 281-308 (1994).
Wijeratne et al., "The present status of electroconvulsive therapy: a systematic review", *MJA* 171: 250-254 (1999).
Folk et al., "Anesthesia for Electroconvulsive Therapy: A Review", *The Journal of ECT*:16:2: 157-170 (2000).
Fogg-Waberski et al., "Electroconvulsive Therapy: Clinical Science vs Controversial Perceptions", *Connecticut Medicine* 64:6: 335-337 (2000).
Datto, "Side Effects of Electroconvulsive Therapy", *Depression and Anxiety* 12: 130-134 (2000).

* cited by examiner

*Primary Examiner*—San-Ming Hui
(74) *Attorney, Agent, or Firm*—Townsend and Townsend and Crew LLP

(57) ABSTRACT

This invention generally pertains to the field of psychiatry. In particular, this invention pertains to the discovery that agents which inhibit the binding of cortisol to the glucocorticoid receptor can be used in methods of increasing the therapeutic response to electroconvulsive therapy ("ECT").

22 Claims, No Drawings

METHODS FOR INCREASING THE THERAPEUTIC RESPONSE TO ELECTROCONVULSIVE THERAPY

FIELD OF THE INVENTION

This invention generally pertains to the field of psychiatry. In particular, this invention pertains to the discovery that agents which inhibit the binding of cortisol to the glucocorticoid receptor can be used to increase the therapeutic response to electroconvulsive therapy ("ECT").

BACKGROUND OF THE INVENTION

ECT is an effective, though controversial treatment, for serious forms of mental illness. There are an estimated 100,000 patients per year in the United Sates who are treated for severe mental disorders with ECT. (See Datto, *Depression and Anxiety*, 12:130134 (2000), Fogg-Waberski et al., *Connecticut Medicine* 64:335-337 (2000), Wijeratne et al., *Medical Journal of Australia*, 171:250-254). ECT treatment involves the administration of an electrical current through the brain in order to induce a controlled seizure. Despite ECT's positive safety record and high level of effectiveness, the risks associated with ECT are considerable. Side effects with varying degrees of severity range from hypertension, arrhythmia, asystole and tachycardia to muscle pain, acute confusional states, persistent memory deficits, fatigue, headaches, and nausea. See Datto, supra, While some medications such as medications to control blood pressure and heart rate have been administered with ECT to reduce side effects, significant risks remain with each ECT treatment. (See Folk et al., *The Journal of ECT*, 16(2) 157-170, (2000))

Steroid hormones are well known to have significant effects on animal cells. Corticosteroids are steroid hormones released by the adrenal glands. The most significant human adrenal corticosteroids are cortisol, corticosterone and aldosterone. Based on their observed effects on carbohydrate, mineral and water metabolism, these compounds have been divided into two classes: the mineralocorticoids, affecting mineral and water metabolism, such as aldosterone; and the glucocorticoids, affecting carbohydrate metabolism, such as corticosterone and cortisol (hydrocortisone, 17-hydroxycorticosterone). Corticosterone can act as both a glucocorticoid and as a mineralocorticoid.

Corticosteroids produce cellular effects following binding to receptors located in the cytoplasm of the cell. Ligand-bound receptors migrate to the nucleus of the cell, where they act on the nuclear material to alter gene expression in the cell. Two general classes of corticosteroid receptors are now recognized, the mineralocorticoid receptors (also termed type I, or MR) and the glucocorticoid receptors (also termed type II, or GR). In addition, it is well known that there are also other steroid receptors which may be present on some animal cells. An example of another steroid hormone receptor is the progesterone receptor.

Mineralcorticoidu receptors (MRs) bind cortisol with ten-fold higher affinity than glucocorticoid receptors (GRs) bind glucocorticoids. Thus, the activation of the two classes of receptors may differ depending on the corticosteroid (cortisol) concentration. Blood levels of the glucocorticoid cortisol vary over a wide range during the day. In general, normal cortisol concentrations in the blood range from about 0.5 nM to about 50 nM; however, in response to stress, cortisol concentration may exceed 100 nM.

Glucocorticoid blockers are agents that block or reduce the effects of glucocorticoids. Such interference with glucocorticoid action may, for example, be due to interference with binding of glucocorticoid agonists to glucocorticoid receptors (GR), or to interference with the action of agonist-bound GR at the cell nucleus, or to interference with expression or processing of gene products induced by the action of agonist-bound GR at the nucleus. Glucocorticoid receptor antagonists (GR antagonists) are compounds which inhibit the effect of the native ligand or of glucocorticoid agonists on GR. One mode of action of GR antagonists is to inhibit the binding of GR ligands to GR. A discussion of glucocorticoid antagonists may be found in Agarwal et al. "Glucocorticoid antagonists", FEBSLett., 217:221-226 (1987). An example of a GR antagonist is mifepristone, (11β, 17β)-11-[4-(dimethylamino) phenyl]-17-hydroxy-17-(1-propynyl)estra-4,9-dien-3-one, also known as RU-486 or RU-38486. See U.S. Pat. No. 4,368,085. Mifepristone binds specifically to GR with high affinity (Kd<10-9 M). This is an affinity about 18 times that of the affinity of cortisol for GR. GR antagonists may be steroids, such as mifepristone, or nonsteroids.

Examples of other steroidal GR antagonists include androgen-type steroid compounds as described in U.S. Pat. No. 5,929,058, and the compounds disclosed in U.S. Pat. Nos. 4,296,206; 4,386,085; 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; 5,616,458, and 5,696,127. Such steroidal GR antagonists include cortexolone, dexamethasoneoxetanone, 19-nordeoxycorticosterone, 19-norprogesterone, cortisol-21-mesylate; dexamethasone-21-mesylate, 11β-(4-dimethylaminoethoxyphenyl)-17α-propynyl-17β-hydroxy-4,9-estradien-3-(RU009), and 17β-hydroxy-17α-19-(4-methylphenyl)androsta-4,9(11)-dien-3-one (RU044).

Examples of other non-steroidal GR antagonists include ketoconazole, clotrimazole; N-(triphenylmethyl)imidazole; N-([2-fluoro-9-phenyl]fluorenyl)imidazole; N([2-pyridyl]diphenylmethyl) imidazole; N-(2-[4,4',4"-trichlorotrityl]oxyethyl)morpholine; 1 (2[4,4',4"-trichlorotrityl]oxyethyl)-4-(2-hydroethyl) dimaleate; N-([4,4',4"]trichlorotrityl) imidazole; 9-(3-mercapto-1,2,4-triazolyl)-9-phenyl-2,7-difluorofluorenone; 1-(2-chlorotrityl)-3,5-dimethylpyrazole; 4-(morpholinomethyl)-A-(2-pyridyl)benzhydrol; 5-(5-methoxy-2-(N-methylcarbamoyl)-phenyl)dibenzosuberol; N-(2-chlorotrityl)-L-prolinol acetate; 1-(2-chlorotrityl)-2-methylimidazole; 1-(2-chlorotrityl)-1,2,4-triazole; 1,S-bis (4,4',4"-trichlorotrityl)-1,2,4-triazole-3-thiol; and N-((2,6-dichloro-3-methylphenyl)diphenyl)methylimidazole (see U.S. Pat. No. 6,051,573); and the GR antagonist compounds disclosed in U.S. Pat. No. 5,696,127; the compounds disclosed in PCT International Application No. WO 96/19458, which describes non-steroidal compounds which are high-affinity, highly selective antagonists for steroid receptors, such as 6-substituted-1,2-dihydro-N-protected-quinolines; and some κ opioid ligands, such as the κ opioid compounds dynorphin-1,13-diamide, U50,488 (trans-(1R, 2R)-3,4-dichloro-N-methyl-N-[2-(1-pyrrolidinal)cyclohexyl]benzeneacetamide), bremazocine and ethylketocyclazocine; and the non-specific opioid receptor ligand, naloxone, as disclosed in Evans et al., *Endocrin.*, 141:2294-2300 (2000).

The present inventors have determined that glucocorticoid receptor antagonists increase the therapeutic response to ECT in a patient. There has been no evidence prior to this invention that an antiglucocorticoid therapy would be desirable in a patient undergoing ECT. Methods of making ECT safer and more widely accepted as an effective treatment for patients suffering from mental illness are needed. By increasing the therapeutic response to ECT in a patient, this invention addresses this and other needs.

BRIEF SUMMARY OF THE INVENTION

This invention is directed to methods for increasing the therapeutic response to ECT in a patient having a disease amenable to ECT. The methods of the present invention include administering an antiglucocorticoid drug and administering ECT to a patient. The amount of antiglucocorticoid administered will be sufficient to increase the therapeutic response to ECT in the patient.

In one aspect of the present invention, an increased therapeutic response to ECT is measured by a reduction in side effects associated with ECT. In one embodiment, side effects side associated with ECT are tachycardia, atrial arrhythmia, ventricular arrhythmia, hypertension, asystole, muscle pain, fatigue, headaches, nausea, amnesia, or confusion.

In a second aspect of the present invention, an increased therapeutic response to ECT is measured by a reduction in the number, length or frequency of ECT treatments necessary to achieve a desired therapeutic effect.

In a third aspect, an increased therapeutic response to ECT is measured by a reduction of electrical intensity or stimulus dosage of ECT treatment necessary to achieve a desired therapeutic effect.

In a fourth aspect of the invention, a disease amenable to ECT includes, for example, melancholic depression, psychotic major depression, mania, schizophrenia, and catatonia.

In a fifth aspect of the invention, an antiglucocorticoid used in the present invention comprises a steroidal skeleton with at least one phenyl-containing moiety in the 11-position of the steroidal skeleton. In one embodiment, the antiglucocorticoid comprises mifepristone.

In a sixth aspect of the invention, an antiglucocorticoid is administered prior to ECT treatment.

In a seventh aspect, an antiglucocorticoid used in the present invention is administered at a rate of 2-20 mg per kilogram of body weight per day for 15 days prior to ECT treatment.

In an eighth aspect, an antiglucocorticoid used in the present invention is administered at a rate of 2-20 mg per kilogram of body weight per day for 7 days prior to ECT treatment.

In an eighth aspect, an antiglucocorticoid used in the present invention is administered at a rate of 600 mg per day for four days prior to ECT treatment.

In a ninth aspect, an antiglucocorticoid is administered on the day of ECT treatment.

In a tenth aspect, an antiglucocorticoid is administered up to four hours before ECT treatment.

In an eleventh aspect of the present invention, an antiglucocorticoid is administered orally.

In a twelfth aspect, the antiglucocorticoid is administered transdermally.

DETAILED DESCRIPTION OF THE INVENTION

I. Introduction

This invention pertains to methods for increasing the therapeutic response to ECT in a patient. ECT is an effective treatment for serious forms of mental illness, e.g., melancholic depression, psychotic major depression, mania, schizophrenia and catatonia. Many theories have been proposed to explain the mechanism of action of ECT and to account for the therapeutic effects of ECT, however, a detailed understanding of why and how ECT exerts its therapeutic effects remains unknown. Nevertheless, the present inventors have discovered that treating a patient with an antiglucocorticoid therapy prior to administration of ECT treatment is an effective way to improve the therapeutic response to ECT in a patient.

Methods of treating patients with ECT are known in the art. Typically, a patient undergoing ECT is administered an average of about 6-12 ECT treatments at a frequency of about 2-3 ECT treatments per week, (See Datto, supra, Olfoon et al., *Am. J Psych* 155:22-24 (1998)). Adjustments may be made depending on the severity and type of disease to be treated. ECT treatment may be broken down into five distinct phases, e.g., preparation, anesthesia induction, administration of stimulus, seizure, and recovery. The preparation stage of ECT treatment involves applying the necessary monitoring equipment to the patient. Standard monitoring equipment includes, for example, equipment for monitoring blood pressure, oxygen saturation and heart rate of the patient. A device to monitor seizure duration may also be employed. Depending upon whether the ECT treatment is unilateral or bilateral, electrodes may be applied unilaterally or bilaterally on the scalp of the patient.

Anesthesia practices used in conjunction with ECT may vary. Typically, anesthetics, e.g., barbiturates, are administered to induce sleep and muscle depolarizing agents are administered to induce paralysis and prevent injury during the seizure. Many different anesthetics or muscle depolarizing agents may be used. The skilled practitioner will know how to administer the appropriate drugs and dosages. For example, Brevital may be used at doses of 1-3 mg/kg. Other barbiturates that may be used include thiopental (Penithal) or Proprofal (Deprivan). Examples of muscle depolarizing agents include succinylcholine. In addition to anesthetic and muscle depolarizing agents, other medications may be administered to counteract the side effects of ECT or anesthesia. For example, drugs to control an increase in blood pressure and heart rate may be administered, as well as drugs to control anesthesia-induced nausea or myalgias.

After the patient is properly prepared and anesthetized, e.g., by methods known in the art, the electrical stimulus may be administered. Any device designed for ECT may be used to administer the electrical stimulus, e.g., specially designed machines that create a bi-directional square wave stimulus train up to 8 seconds in length. The practitioner will know how to alter parameters on the ECT device, e.g., pulse width, frequency, stimulus duration, for use with a particular patient, e.g., the minimum energy required to induce a generalized seizure may be determined by gradually increasing the stimulus dose. The minimum dose for bilateral treatment may be increased by a factor of 2.5-6 times for unilateral treatments.

The seizure induced by ECT is indistinguishable from a generalized tonic-clonic seizure seen in epilepsy. ECT induced seizures produce the classic spike and wave waveform on an EEG. An ECT induced seizure, however, is controlled, e.g., muscle depolarizing agents reduce the muscle contractions usually associated with seizures, bite blocks placed in the patient's mouth prevent dental injury caused by the tonic contraction of the massaters, an oxygen mask prevents hypoxia. Typically, the seizure will have a duration of 15 to 120 seconds.

After the seizure, a recovery period begins where vital signs are monitored and additional medication may be administered to control increased blood pressure, heart rate or other side effects of treatment.

Using the methods of the present invention, a patient undergoing ECT will be treated with antiglucocorticoids. Administration of an antiglucocorticoid prior to application of the electrical stimulus for ECT treatment will increase the therapeutic response in the patient to ECT. By administering an antiglucocorticoid prior to ECT treatment, e.g., prior to application of the electrical stimulus, side effects associated with ECT may be lessened or diminished in the patient. For example, a patient treated by the methods of the present invention may experience less confusion and memory impairment after ECT treatment than if the patient had been treated with ECT alone. A patient treated by the methods of the present invention, may also respond faster to ECT. For example, using the methods of the present invention, a patient may experience an improved mental state and well-being after ECT treatment. Fewer, less frequent, or shorter ECT treatments may be administered to the patient. The methods of the present invention therefore improve the efficacy and safety of ECT, e.g., by reducing negative side effects, by reducing frequency, length, or number of treatments, or by reducing the electrical intensity of treatment.

II. Defintions

The term "psychotic major depression," also referred to as "psychotic depression" (Schatzberg (1992) *Am. J. Psychiatry* 149:733-745), "psychotic (delusional) depression" (Ibid.), "delusional depression" (Glassman (1981) supra) and, "major depression with psychotic features" (see the DSM-III-R), refers to a distinct psychiatric disorder which includes both depressive and psychotic features. Individuals manifesting both depression and psychosis, i.e. psychotic depression, are herein referred to as "psychotic depressives." It has been long-recognized in the art as a distinct syndrome, as described, for example, by Schatzberg (1992) supra. Illustrative of this distinctness are studies which have found significant differences between patients with psychotic and nonpsychotic depression in glucocorticoid activity, dopamine-beta-hydroxylase activity, levels of dopamine and serotonin metabolites, sleep measures and ventricle to brain ratios. Psychotic depressives respond very differently to treatment compared to individuals with other forms of depression, such as "non-psychotic major depression." Psychotic depressives have a low placebo response rate and a respond poorly to antidepressant therapy alone (without concurrent anti-psychotic treatment). Psychotic depressives are markedly unresponsive to tricyclic (antidepressive) drug therapy (Glassman, et al. (1975) supra). Clinical manifestations and diagnostic parameters of "psychotic major depression" are described in detail in the DSM-IV (see fourth edition of Diagnostic and Statistical Manual of Mental Disorders (1994) Task Force on DSM-IV, American Psychiatric Association ("DSM-IV"); Kaplan, Ed. (1995) Comprehensive Textbook of Psychiatry/VI, vol. 1, sixth ed., pp 621-627, Williams & Wilkins, Balt., Md.). Thus, due to its unique pathophysiology, high rate of morbidity and response to treatment, there is great practical need to differentially diagnose and specifically treat psychotic major depression as compared to non-psychotic depression.

The term schizophrenia refers to a distinct psychiatric disorder characterized by a range of cognitive and emotional dysfunctions that include perception, inferential thinking, language and communication, behavioral monitoring, affect, fluency and productivity of thought and speech, hedonic capacity, volition and drive, and attention. The active-phase symptoms of schizophrenia include delusions, hallucinations, disorganized speech, grossly disorganized behavior, catatonic behavior, and negative symptoms as described in DSM-IV. Further clinical manifestations and diagnostic parameters of "schizophrenia" are described in detail in the DSM-IV (Kaplan, ed. (1995) supra).

Melancholic depression specifies a distinct type of depression wherein an individual exhibits a loss of interest or pleasure in all, or almost all, activities or a lack of reactivity to usually pleasurable stimuli as described in DSM-IV. Further clinical manifestations and diagnostic parameters of "melancholic depression" are described in detail in the DSM-IV (Kaplan, ed. (1995) supra).

The term "mania" refers to a psychotic disorder wherein an individual possesses an abnormally and persistently elevated, expansive or irritable mood. The abnormal mood will last at least one week and will be accompanied by other symptoms including inflated self-esteem, grandiosity, decreased need for sleep, pressure of speech, flight of ideas, distractibility, increased involvement in goal-directed activities or psychomotor agitation, and increased involvement in pleasurable activities with a high potential for painful consequences as described in DSM-IV. Further clinical manifestations and diagnostic parameters of "mania" or "manic episodes" are described in detail in the DSM-IV (Kaplan, ed. (1995) supra).

The term "catatonia" refers to a psychotic disorder wherein an individual possesses catatonic features including motoric immobility, excessive motor activity, extreme negativism, peculiarities of voluntary movement and echolalia or echopraxia. Further clinical manifestations and diagnostic parameters of "catatonia" or "catatonic episodes" are described in detail in the DSM-IV (Kaplan, ed. (1995) supra).

"Electroconvulsive therapy ("ECT") is a treatment for severe mental illness in which a brief application of electrical current is applied to an individual. The electrical current passes through the brain of the individual thereby activating it and producing a generalized seizure.

A patient "having a disease amenable to electroconvulsive therapy" refers to a patient having a severe mental disorder. Typically, the patient does not respond well to conventional therapy, e.g., drug therapy including the administration of anti-psyhctoic drugs, antidepressants and even antiglucocorticoids. A person having a disease amenable to ECT has all the appropriate indicators that signal to a mental health professional that ECT therapy is an appropriate course of treatment. These indicators may include having any one of the following diseases: melancholic depression, psychotic major depression, mania, schizophrenia, and catatonia. Individuals who are at an increased risk of suicide, suffer from acute episodes of mental disorders, display nonresponsiveness to drug therapy, or have intense suffering or incapacitation may be indicative of patients having a disease amenable to ECT. A skilled practitioner will know how to determine whether an individual has a disease amenable to ECT and is thus treatable by the methods of the present invention.

Severe mental disorders may include disorders such as melancholic depression, psychotic major depression, mania, schizophrenia, and catatonia. Conventional drug therapies include an anti-psychotic or anti-depressant therapy regime.

The term "increasing the therapeutic response to ECT" refers to an indicia of success in ECT treatment of a disease amenable to ECT, including any objective or subjective parameter such as abatement, remission or diminishing of symptoms or an improvement in a patient's physical or mental well-being. Amelioration of symptoms can be based on objective or subjective parameters: including the results of a physical examination and/or a psychiatric evaluation. For example, a clinical guide to monitor the effective amelioration of a mental disorder, such as psychotic major depression or melancholic depression, is found in the Structured Clinical Interview for DSM-IV Axis I mood disorders ("SCID-P") (Kaplan, ed. (1995) supra)).

"Increasing the therapeutic response to ECT" may be achieved by decreasing the severity or occurrence of side effects typically associated with ECT. Side effects associated with ECT include any negative effect that is a by-product of ECT treatment. Negative side effects, for example, include tachycardia, atrial arrhythmia, ventricular arrhythmia, hypertension, asystole, muscle pain, fatigue, headaches, nausea, amnesia, and confusion.

An individual treated by the methods of the present invention who exhibits an "increased therapeutic response to ECT" may be placed on a modified ECT treatment schedule that consists of fewer, less frequent, or shorter ECT treatments. A modification of ECT treatment includes any modification that would render ECT safer to administer to an individual including, for example, a reduction in the electrical intensity or stimulus dosage of ECT.

The term "cortisol" refers to a family of compositions also referred to hydrocortisone, and any synthetic or natural analogues thereof.

The term "glucocorticoid receptor" ("GR") refers to a family of intracellular receptors also referred to as the cortisol receptor, which specifically bind to cortisol and/or cortisol analogs. The term includes isoforms of GR, recombinant GR and mutated GR.

The term "mifepristone" refers to a family of compositions also referred to as RU486, or RU38.486, or 17-beta-hydroxy-11-beta-(4-dimethyl-aminophenyl)-17-alpha-(1-propynyl)-estra-4,9-dien-3-one), or 11-beta-(4-dimethyl-aminophenyl)-17-beta-hydroxy-17-alpha-(1-propynyl)-estra-4,9-dien-3-one), or analogs thereof, which bind to the GR, typically with high affinity, and inhibit the biological effects initiated/mediated by the binding of any cortisol or cortisol analogue to a GR receptor. Chemical names for RU-486 vary; for example, RU486 has also been termed: 11B-[p-(Dimethylamino)phenyl]17B-hydroxy-17-(1-propynyl)-estra-4,9-dien-3-one; 11B-(4-dimethyl-aminophenyl) 17B-hydroxy-17A-(prop-1-ynyl)-estra-4,9-dien-3-one; 17B-hydroxy-11B-(4-dimethylaminophenyl-1)-17A-(propynyl-1)-estra-4,9-diene-3-one; 17B-hydroxy-11B-(4-dimethylaminophenyl-1)-17A-(propynyl-1)-E; (11B, 17B)-11-[4-dimethylamino)-phenyl]-17-hydroxy-17-(1-propynyl) estra-4,9-dien-3-one; and 11B-[4-(N,N-dimethylamino) phenyl]17A-(prop-1-ynyl)-D-4,9-estradiene-17B-ol-3-one.

The term "specific glucocorticoid receptor antagonist" or "antiglucocorticoid" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" also refers to any composition or compound which inhibits any biological response associated with the binding of a GR to an agonist. By "specific", we intend the drug to preferentially bind to the GR rather than the mineralocorticoid receptor (MR) at a rate of at least 100-fold, and frequently 1000-fold.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N-methylglucamine, and the like. Such salts also include acid addition salts formed with inorganic acids (e.g. hydrochloric and hydrobromic acids) and organic acids (e.g. acetic acid, citri c acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g. $C_{1-6}$ alkyl esters. When there are two acidic groups present, a pharmaceutically acceptable salt or ester may be a mono-acid-mono-salt or ester or a di-salt or ester; and similarly where there are more than two acidic groups present, some or all of such groups can be salified or esterified. Compounds named in this invention may be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

An "antiglucocorticoid therapy" refers to administration of antiglucocorticoids to a patient.

A "therapeutically effective amount" means an amount that, when administered to a patient for treating a disease, is sufficient to effect treatment for that disease. In the case of a therapeutically effective amount of an antiglucocorticoid for increasing the therapeutic response to ECT, the therapeutically effective amount of the antiglucocorticoid will be an amount necessary to effect an increase in therapeutic response to ECT. The response can be measured by an improved mental well-being of the patient, a decrease in side effects associated with ECT or a decrease in the amount or intensity of ECT treatment necessary to effectuate a therapeutic response. Thus, an antiglucocorticoid administered with ECT will be effective in achieving a therapeutic response to ECT that is greater than the therapeutic response achievable by ECT treatment alone.

Administration of antiglucocorticoid "prior to ECT treatment" means administration of the antiglucocorticoid such that the antiglucocorticoid is present in the blood during administration of each ECT treatment at such a level that the antiglucocorticoid can effectuate an increase in the therapeutic response to ECT in the patient. For example, an antiglucocorticoid may be administered 14 days prior to an ECT treatment, 7 days prior to an ECT treatment, or 1 day prior to ECT treatment. An antiglucocorticoid may be administered 1-14 days before ECT treatment. An antiglucocorticoid may also be administered on the day of ECT treatment. For example, an antiglucocorticoid therapy may be administered before applying monitoring equipment to the patient, during the preparation stage of ECT or during the anesthesia stage of the ECT. An antiglucocorticoid may be administered 1-6 hours before the administration of the electrical stimulus. A person of ordinary skill in the art, having knowledge of ECT and glucocorticoid blockers, would have no difficulty determining the appropriate timing, sequence and dosage of administration of glucocorticoid blockers such that the glucocorticoid blocker is present in the patient at the appropriate dosage during ECT treatment.

III. Glucocorticoid Receptor Antagonists to Increase the Therapeutic Response to ECT The invention provides for methods of increasing the therapeutic response to ECT in a patient utilizing any composition or compound that can block a biological response associated with the binding of cortisol or a cortisol analogue to a GR. Antagonists of GR activity utilized in the methods of the invention are well described in the scientific and patent literature. A few illustrative examples are set forth below.

A. Steroidal Anti-Glucocorticoids as GR Antagonists.

Steroidal glucocorticoid antagonists are administered for increasing the therapeutic response to ECT in a patient in various embodiments of the invention. Steroidal antiglucocorticoids can be obtained by modification of the basic structure of glucocorticoid agonists, i.e., varied forms of the steroid backbone. The structure of cortisol can be modified in a variety of ways. The two most commonly known classes of structural modifications of the cortisol steroid backbone to create glucocorticoid antagonists include modifications of the 11-beta hydroxy group and modification of the 17-beta side chain (see, e.g., Lefebvre, *J. Steroid Biochem.* 33:557-563, 1989).

(i) Removal or Substitution of the 11-beta Hydroxy Group

Glucocorticoid agonists with modified steroidal backbones comprising removal or substitution of the 11-beta hydroxy group are administered in one embodiment of the invention. This class includes natural antiglucocorticoids, including cortexolone, progesterone and testosterone derivatives, and synthetic compositions, such as mifepristone (Lefebvre, et al. Ibid). Preferred embodiments of the invention include all 11-beta-aryl steroid backbone derivatives because these compounds are devoid of progesterone receptor (PR) binding activity (Agarwal *FEBS* 217:221-226, 1987). Another preferred embodiment comprises an 11-beta phenyl-aminodimethyl steroid backbone derivative, i.e., mifepristone, which is both an effective anti-glucocorticoid and anti-progesterone agent. These compositions act as reversibly-binding steroid receptor antagonists. For example, when bound to a 11-beta phenyl-aminodimethyl steroid, the steroid receptor is maintained in a conformation that cannot bind its natural ligand, such as cortisol in the case of GR (Cadepond, 1997, supra).

Synthetic 11-beta phenyl-aminodimethyl steroids include mifepristone, also known as RU486, or 17-beta-hydrox-11-beta-(4-dimethyl-aminophenyl)17-alpha-(1-propynyl)estra-4,9-dien Mifepristone has been shown to be a powerful antagonist of both the progesterone and glucocorticoid (GR) receptors. Another 11-beta phenylaminodimethyl steroids shown to have GR antagonist effects includes RU009 (RU39.009), 11-beta-(4-dimethyl-aminoethoxyphenyl)-17-alpha-(propynyl-17-beta-hydroxy-4,9-estradien-3-one) (see Bocquel, *J. Steroid Biochem. Molec. Biol.* 45:205-215, 1993). Another GR antagonist related to RU486 is RU044 (RU43.044)17-beta-hydrox-17-alpha-19-(4-methylphenyl)-androsta-4,9 4,9(11)-dien-3-one) (Bocquel, 1993, supra). See also Teutsch, *Steroids* 38:651-665, 1981; U.S. Pat. Nos. 4,386,085 and 4,912,097.

One embodiment includes compositions containing the basic glucocorticoid steroid structure which are irreversible anti-glucocorticoids. Such compounds include alpha-keto-methanesulfonate derivatives of cortisol, including cortisol-21-mesylate (4-pregnene-11-beta, 17-alpha, 21-triol-3, 20-dione-21-methane-sulfonate and dexamethasone-21-mesylate (16-methyl-9 alpha-fluoro-1,4-pregnadiene-11-beta, 17-alpha, 21-triol-3, 20-dione-21-methane-sulfonate). See Simons, *J Steroid Biochem.* 24:25-32 1986; Mercier, *J Steroid Biochem.* 25:11-20, 1986; U.S. Pat. No. 4,296,206.

(ii) Modification of the 17-beta Side Chain Group

Steroidal antiglucocorticoids which can be obtained by various structural modifications of the 17-beta side chain are also used in the methods of the invention. This class includes synthetic antiglucocorticoids such as dexamethasone-oxetanone, various 17, 21-acetonide derivatives and 17-beta-carboxamide derivatives of dexamethasone (Lefebvre, 1989, supra; Rousseau, *Nature* 279:158-160, 1979).

(iii) Other Steroid Backbone Modifications

GR antagonists used in the various embodiments of the invention include any steroid backbone modification which effects a biological response resulting from a GR-agonist interaction. Steroid backbone antagonists can be any natural or synthetic variation of cortisol, such as adrenal steroids missing the C-19 methyl group, such as 19-nordeoxycorticosterone and 19-norprogesterone (Wynne, *Endocrinology* 107:1278-1280, 1980).

In general, the 11-beta side chain substituent, and particularly the size of that substituent, can play a key role in determining the extent of a steroid's antiglucocorticoid activity. Substitutions in the A ring of the steroid backbone can also be important. 17-hydroxypropenyl side chains generally decrease antiglucocorticoidal activity in comparison to 17-propinyl side chain containing compounds.

B. Non-Steroidal Anti-Glucocorticoids as Antagonists

Non-steroidal glucocorticoid antagonists are also used in the methods of the invention to treat MCI. These include synthetic mimetics and analogs of proteins, including partially peptidic, pseudopeptidic and non-peptidic molecular entities. For example, oligomeric peptidomimetics useful in the invention include (alpha-beta-unsaturated) peptidosulfonamides, N-substituted glycine derivatives, oligo carbamates, oligo urea peptidomimetics, hydrazinopeptides, oligosulfones and the like (see, e.g., Amour, Int. *J Pept. Protein Res.* 43:297-304, 1994; de Bont, *Bioorganic & Medicinal Chem.* 4:667-672, 1996). The creation and simultaneous screening of large libraries of synthetic molecules can be carried out using well-known techniques in combinatorial chemistry, for example, see van Breemen, *Anal Chem* 69:2159-2164, 1997; and Lam, *Anticancer Drug Des* 12:145-167, 1997. Design of peptidomimeties specific for GR can be designed using computer programs in conjunction with combinatorial chemistry (combinatorial library) screening approaches (Murray, *J. of Computer-Aided Molec. Design* 9:381-395, 1995; Bohm, *J. of Computer-Aided Molec. Design* 10:265-272, 1996). Such "rational drug design" can help develop peptide isomerics and conformers including cycloisomers, retro-inverso isomers, retro isomers and the like (as discussed in Chorev, *TibTech* 13:438-445, 1995).

C. Identifying Specific Glucocorticoid Receptor Antagonists

Because any specific GR antagonist can be in the methods of the invention, in addition to the compounds and compositions described above, additional useful GR antagonists can be determined by the skilled artisan. A variety of such routine, well-known methods can be used and are described in the scientific and patent literature. They include in vitro and in vivo assays for the identification of additional GR antagonists. A few illustrative examples are described below.

One assay that can be used to identify a GR antagonist of the invention measures the effect of a putative GR antagonist on tyrosine amino-transferase activity in accordance with the method of Granner, *Meth. Enzymol.* 15:633, 1970. This analysis is based on measurement of the activity of the liver enzyme tyrosine amino-transferase (TAT) in cultures of rat hepatoma cells (RHC). TAT catalyzes the first step in the metabolism of tyrosine and is induced by glucocorticoids (cortisol) both in liver and hepatoma cells. This activity is easily measured in cell extracts. TAT converts the amino group of tyrosine to 2-oxoglutaric acid. P-hydroxyphenylpyruvate is also formed. It can be converted to the more stable p-hydroxybenzaldehyde in an alkaline solution and quantitated by absorbance at 331 nm. The putative GR antagonist is co-administered with cortisol to whole liver, in vivo or ex vivo, or hepatoma cells or cell extracts. A compound is identified as a GR antagonist when its administration decreases the amount of induced TAT activity, as compared to control (i.e., only cortisol or GR agonist added) (see also Shirwany, *Biochem. Biophys. Acta* 886:162-168, 1986).

Further illustrative of the many assays which can be used to identify compositions utilized in the methods of the invention, in addition to the TAT assay, are assays based on glucocorticoid activities in vivo. For example, assays that assess the ability of a putative GR antagonist to inhibit uptake of $^3$H-thymidine into DNA in cells which are stimulated by glucocorticoids can be used. Alternatively, the putative GR antagonist can complete with $^3$H-dexamethasone for binding to a hepatoma tissue culture GR (see, e.g., Choi, et al., *Steroids* 57:313-318, 1992). As another example, the ability of a putative GR antagonist to block nuclear binding of $^3$H-dexamethasone-GR complex can be used (Alexandrova et al., *J Steroid Biochem. Mol. Biol.* 41:723-725, 1992). To further identify putative GR antagonists, kinetic assays able to discriminate between glucocorticoid agonists and antagonists by means of receptor-binding kinetics can also be used (as described in Jones, *Biochem J.* 204:721-729, 1982).

In another illustrative example, the assay described by Daune, *Molec. Pharm.* 13:948-955, 1977; and in U.S. Pat. No. 4,386,085, can be used to identify antiglucocorticoid activity. Briefly, the thymocytes of surrenalectomized rats are incubated in nutritive medium containing dexamethasone with the test compound (the putative GR antagonist) at varying concentrations. $^3$H-uridine is added to the cell culture, which is further incubated, and the extent of incorporation of radiolabel into polynucleotide is measured. Glucocorticoid agonists decrease the amount of $^3$H-uridine incorporated. Thus, a GR antagonist will oppose this effect.

For additional compounds that can be utilized in the methods of the invention and methods of identifying and making such compounds, see U.S. Pat. Nos, 4,296,206 (see above); 4,386,085 (see above); 4,447,424; 4,477,445; 4,519, 946; 4,540,686; 4,547,493; 4,634,695; 4,634,696; 4,753, 932; 4,774,236; 4,808,710; 4,814,327; 4,829,060; 4,861, 763; 4,912,097; 4,921,638; 4,943,566; 4,954,490; 4,978, 657; 5,006,518; 5,043,332; 5,064,822; 5,073,548; 5,089, 488; 5,089,635; 5,093,507; 5,095,010; 5,095,129; 5,132, 299; 5,166,146; 5,166,199; 5,173,405; 5,276,023; 5,380, 839; 5,348,729; 5,426,102; 5,439,913; and 5,616,458; and WO 96/19458, which describes non-steroidal compounds which are high-affinity, highly selective modulators (antagonists) for steroid receptors, such as 6-substituted-1,2-dihydro N–1protected quinolines.

The specificity of the antagonist for the GR relative to the MR can be measured using a variety of assays known to those of skill in the art. For example, specific antagonists can be identified by measuring the ability of the antagonist to bind to the GR compared to the MR (see, e.g., U.S. Pat. Nos. 5,606,021; 5,696,127; 5,215,916; 5,071,773). Such an analysis can be performed using either direct binding assay or by assessing competitive binding to the purified GR or MR in the presence of a known antagonist. In an exemplary assay, cells that are stably expressing the glucocorticod receptor or mineralocorticoid receptor (see, e.g., U.S. Pat. No. 5,606,021) at high levels are used as a source of purified receptor. The affinity of the antagonist for the receptor is then directly measured. Those antagonists that exhibit at least a 100-fold higher affinity, often 1000-fold, for the GR relative to the MR are then selected for use in the methods of the invention.

A GR-specific antagonist may also be defined as a compound that has the ability to inhibit GR-mediated activities, but not MR-mediated activities. One method of identifying such a GR-specific antagonist is to assess the ability of an antagonist to prevent activation of reporter constructs using transfection assays (see, e.g., Bocquel et al, *J Steroid Biochem Molec. Biol.* 45:205-215, 1993, U.S. Pat. Nos. 5,606, 021, 5,929,058). In an exemplary transfection assay, an expression plasmid encoding the receptor and a reporter plasmid containing a reporter gene linked to receptor-specific regulatory elements are cotransfected into suitable receptor-negative host cells. The transfected host cells are then cultured in the presence and absence of a hormone, such as cortisol or analog thereof, able to activate the hormone responsive promoter/enhancer element of the reporter plasmid. Next the transfected and cultured host cells are monitored for induction (i.e., the presence) of the product of the reporter gene sequence. Finally, the expression and/or steroid bindingcapacity of the hormone receptor protein (coded for by the receptor DNA sequence on the expression plasmid and produced in the transfected and cultured host cells), is measured by determining the activity of the reporter gene in the presence and absence of an antagonist. The antagonist activity of a compound may be determined in comparison to known antagonists of the GR and MR receptors (see, e.g., U.S. Pat. No. 5,696,127). Efficacy is then reported as the percent maximal response observed for each compound relative to a reference antagonist compound. A GR-specific antagonist is considered to exhibit at least a 100-fold, often 1000-fold or greater, activity towards the GR relative to the MR.

IV. Increasing The Therapeutic Response to ECT Using Glucocorticoid Receptor Antagonists Antiglucocorticoids, such as mifepristone, are formulated as pharmaceuticals to be used in the methods of the invention to increase the therapeutic response to ECT in a patient having a disease amenable to ECT. Any composition or compound that can block a biological response associated with the binding of cortisol or a cortisol analogue to a GR can be used as a pharmaceutical in the invention. Routine means to determine GR antagonist drug regimens and formulations to practice the methods of the invention are well described in the patent and scientific literature, and some illustrative examples are set forth below.

A. Glucocorticoid Receptor Antagonists as Pharmaceutical Compositions

The GR antagonists used in the methods of the invention can be administered by any means known in the art, e.g., parenterally, topically, orally, or by local administration, such as by aerosol or transdermally. The methods of the invention provide for prophylactic and/or therapeutic treatments. The GR antagonists as pharmaceutical formulations can be administered in a variety of unit dosage forms depending upon the condition or disease and the degree of dementia, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

GR antagonist pharmaceutical formulations can be prepared according to any method known to the art for the manufacture of pharmaceuticals. Such drugs can contain sweetening agents, flavoring agents, coloring agents and preserving agents. Any GR antagonist formulation can be admixtured with nontoxic pharmaceutically acceptable excipients which are suitable for manufacture.

Pharmaceutical formulations for oral administration can be formulated using pharmaceutically acceptable carriers well known in the art in appropriate and suitable dosages. Such carriers enable the pharmaceutical formulations to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be obtained through combination of GR antagonist compounds with a solid excipient, optionally grinding a resulting mixture, and processing the mixture of granules, after adding suitable additional compounds, if desired, to obtain tablets or dragee cores. Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain GR antagonist mixed with a filler or binders such as lactose or starches, lubricants such as talc or magnesium stearate, and, optionally, stabilizers. In soft capsules, the GR antagonist compounds may be dissolved or suspended in suitable liquids, such as fatty oils, liquid paraffin, or liquid polyethylene glycol with or without stabilizers.

Aqueous suspensions of the invention contain a GR antagonist in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a GR antagonist in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Dispersible powders and granules of the invention suitable for preparation of an aqueous suspension by the addition of water can be formulated from a GR antagonist in admixture with a dispersing, suspending and/or wetting agent, and one or more preservatives. Suitable dispersing or wetting agents and suspending agents are exemplified by those disclosed above. Additional excipients, for example, sweetening, flavoring and coloring agents, can also be present.

The GR antagonists of this invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The GR antagonists of this invention can also be administered by in intranasal, intraocular, intravaginal, and intrarectal routes including suppositories, insufflation, powders and aerosol formulations (for examples of steroid inhalants, see Rohatagi, *J Clin. Pharmacol.* 35:1187-1193, 1995; Tjwa, *Ann. Allergy Asthma Immunol.* 75:107-111, 1995).

The GR antagonists of the invention can be delivered by transdermally, by a topical route, formulated as applicator sticks, solutions, suspensions, emulsions, gels, creams, ointments, pastes, jellies, paints, powders, and aerosols.

The GR antagonists of the invention can also be delivered as microspheres for slow release in the body. For example, microspheres can be administered via intradermal injection of drug (e.g., mifepristone)-containing microspheres, which slowly release subcutaneously (see Rao, *J Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J Pharm. Pharmacol.* 49:669-674, 1997). Both transdermal and intradermal routes afford constant delivery for weeks or months.

The GR antagonist pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5, that is combined with buffer prior to use In another embodiment, the GR antagonist formulations of the invention are useful for parenteral administration, such as intravenous (IV) administration or administration into a body cavity or lumen of an organ. The formulations for administration will commonly comprise a solution of the GR antagonist (e.g., mifepristone) dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of GR antagonist in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the GR antagonist formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR antagonist into the target cells in vivo. (See, e.g., AlMuhammed, *J Microencapsul.* 13:293-306, 1996; Chonn, *Curr. Opin. Biotechnol.* 6:698708, 1995; Ostro, *Am. J Hosp. Pharm.* 46:1576-1587, 1989).

B. Determining Dosing Regimens for Glucocorticoid Receptor Antagonists

The methods of the invention increase the therapeutic response to ECT in a patient, e.g., improving the mental state of the patient or decreasing the side effects typically associated with ECT. The amount of GR antagonist adequate to accomplish this is defined as a "therapeutically effective dose". The dosage schedule and amounts effective for this use, i.e., the "dosing regimen," will depend upon a variety of factors, including the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the GR antagonists' rate of absorption, bioavailability, metabolism, clearance, and the like (see, e.g., Hidalgo-Aragones (1996) *J Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J Clin. Pharmacol.* 24:103-108; the latest Remington's, supra). For example, in one study, less than 0.5% of the daily dose of mifepristone was excreted in the urine; the drug bound extensively to circulating albumin (see Kawai (1989) supra). The state of the art allows the clinician to determine the dosage regimen for each individual patient, GR antagonist and disease or condition treated. As an illustrative example, the guidelines provided below for mifepristone can be used as guidance to determine the dosage regiment, i.e., dose schedule and dosage levels, of any GR antagonist administered when practicing the methods of the invention.

Single or multiple administrations of GR antagonist formulations can be administered depending on the dosage and frequency as required and tolerated by the patient. The formulations should provide a sufficient quantity of active agent, i.e., mifepristone, to effectively treat the dementia. Thus, one typical pharmaceutical formulations for oral administration of mifepristone is in a daily amount of between about 0.5 to about 20 mg per kilogram of body weight per day. In an alternative embodiment, dosages are from about 1 mg to about 4 mg per kg of body weight per patient per day are used. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable GR antagonist formulations will be known or apparent to those skilled in the art and are described in more detail in such publications as Remington's, supra. See also Nieman, In "Receptor Mediated Antisteroid Action," Agarwal, et al., eds., De Gruyter, N.Y. (1987).

After a pharmaceutical comprising a GR antagonist of the invention has been formulated in a acceptable carrier, it can be placed in an appropriate container and labeled for treatment with ECT. For administration of GR antagonists, such labeling would include, e.g., instructions concerning the amount, frequency and method of administration.

C. Determining Parameters for ECT Therapy for use with Antiglucocorticoids

Using the methods of the present invention, the therapeutic response to ECT in a patient will be increased. In some embodiments of the invention, an increased therapeutic response will result in the administration of fewer ECT treatments. For example, currently, an average of 6-12 treatments are administered to treat an acute depressive episode at a frequency of 2-3 treatments a week. In one embodiment of the present invention, fewer treatments or less frequent treatments may achieve the desired therapeutic effect, e.g. an average of 3-10 treatments administered at a frequency of 1-3 treatments every two weeks. In a second embodiment of the present invention, the methods of the present invention may require the same number and frequency of treatments but the patient may have an improved mental-state than if the patient had been treated with ECT alone. In a third embodiment, the number and frequency of the treatments may remain the same but the side effects associated with ECT may be lessened, for example, a patient may exhibit less confusion. In a fourth embodiment of the present invention, ECT parameters may be adjusted. For example, currently, a pulse width of 0.5 to 2 msec, a frequency of 1-20 Hz and a seizure length of 15-120 seconds is used to administer the electrical current through the brain. Using the methods of the present invention, pulse width may be reduced, frequency may be reduced, and seizure length may be reduced. In a fifth embodiment, electrical intensity or stimulus dosage of ECT treatment may be reduced.

The skilled practitioner, will know how to determine if a patient has an increased therapeutic response to ECT, e.g., by examining the patient, and will be able to adjust ECT treatment accordingly.

It is understood that the examples and embodiments described herein are for illustrative purposes only and that various modifications or changes in light thereof will be suggested to persons skilled in the art and are to be included within the spirit and purview of this application and scope of the appended claims.

All publications and patent applications cited in this specification are herein incorporated by reference as if each individual publication or patent application were specifically and individually indicated to be incorporated by reference.

EXAMPLES

Example 1

Treating Mental Illness with Antiglucocorticoid Therapy Followed by ECT

A patient undergoing mifepristone therapy was not significantly improving. The patient subsequently underwent four treatments of bilateral ECT while continuing mifepristone therapy. Before the fifth treatment, the patient was dramatically improved. He experienced some impairment in short term memory but otherwise had no side-effects from this treatment modality. During each treatment session, the patient received between 60 and 100 mg of methohexital and between 60 and 80 mg of succinylcholine.

For the first ECT treatment, the patient was delivered a stimulus using the Thymatron ECT device at 35% with 45 second eeg seizure duration and 115 second motor duration. After the first treatment, the patient was better able to organize his thoughts and was able to engage in more appropriate conversations. The second treatment was also at 35%, but the eeg duration decreased to 61 seconds and no motor seizure was detected. Consequently on the third treatment, the energy setting was increased to 40% with 115 second eeg duration and 91 second motor duration. After the third treatment, the patient had fewer somatic delusions, was able to comprehend written text and was easier to engage in conversation. On the fourth treatment, no seizure was observed at 40% or 45%. A third stimulation at 70% resulted in a 33 second motor duration and a 84 second eeg duration.

What is claimed is:

1. A method for increasing the therapeutic response to electroconvulsive therapy ("ECT") in a patient having a disease amenable to ECT and non-responsive to antiglucocorticoid drug therapy where said method comprises administering an antiglucocorticoid drug and administering ECT to the patient, wherein the amount of antiglucocorticoid administered is sufficient to increase the therapeutic response to ECT in the patient.

2. The method of claim 1, wherein an increased therapeutic response to ECT is measured by a reduction in the acute confusional state associated with ECT.

3. The method of claim 1, wherein an increased therapeutic response to ECT is measured by a reduction in the number, length or frequency of ECT treatments necessary to achieve a desired therapeutic effect.

4. The method of claim 1, wherein an increased therapeutic response to ECT is measured by a reduction of electrical intensity or stimulus dosage of ECT treatment necessary to achieve a desired therapeutic effect.

5. The method of claim 1, wherein the disease is selected from the group consisting of melancholic depression, psychotic major depression, mania, schizophrenia, and catatonia.

6. The method of claim 5, wherein the disease is melancholic. depression.

7. The method of claim 5, wherein the disease is psychotic major depression.

8. The method of claim 5, wherein the disease is mania.

9. The method of claim 5, wherein the disease is schizophrenia.

10. The method of claim 5, wherein the disease is catatonia.

11. The method of claim 1, wherein the antiglucocorticoid drug comprises a steroidal skeleton with at least one phenyl-containing moiety in the 11-position of the steroidal skeleton.

12. The method of claim 11, wherein the antiglucocorticoid drug comprises mifepristone.

13. The method of claim 1, wherein the antiglucocorticoid drug is administered prior to ECT treatment.

14. The method of claim 13, wherein the antiglucocorticoid drug is administered at a rate of 2-20 mg per kilogram of body weight per day for 15 days prior to ECT treatment.

15. The method of claim 13, wherein the antiglucocorticoid drug is administered at a rate of 2-20 mg per kilogram of body weight per day for 7 days prior to ECT treatment.

16. The method of claim 13, wherein the antiglucocorticoid drug is administered at a rate of 600 mg per day for four days prior to ECT treatment.

17. The method of claim 13, wherein the antiglucocorticoid drug is administered on the day of ECT treatment.

18. The method of claim 13, wherein the antiglucocorticoid drug is administered up to 4 hours before ECT treatment.

19. The method of claim 1, wherein the antiglucocorticoid drug is administered orally.

20. The method of claim 1, wherein the antiglucocorticoid drug is administered transdermally.

21. The method of claim 1, wherein an increased therapeutic response to ECT is measured by a reduction in memory impairment associated with ECT.

22. The method of claim 1, wherein the antiglucocorticoid drug is a specific antiglucocorticoid receptor antagonist.

* * * * *